(12) United States Patent
McDonough et al.

(10) Patent No.: US 6,402,681 B1
(45) Date of Patent: Jun. 11, 2002

(54) PHOTOTHERAPY APPARATUS

(75) Inventors: Robert M. McDonough, Hatfield; Richard Hude, Fairless Hills, both of PA (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 09/520,239

(22) Filed: Mar. 7, 2000

(51) Int. Cl.⁷ .............................................. A61G 11/00
(52) U.S. Cl. ............................. 600/22; 607/88; 362/130
(58) Field of Search ........................ 600/21–22; 307/88, 307/90; 362/130

(56) References Cited

U.S. PATENT DOCUMENTS

| | | |
|---|---|---|
| 547,359 A | 10/1895 | Rimington |
| 1,544,973 A | 7/1925 | Ghadiali |
| 1,563,074 A | 11/1925 | Catlin |
| 2,003,527 A | 6/1935 | Bacon et al. |
| 2,273,316 A | 2/1942 | Goerg et al. |
| 3,822,706 A | 7/1974 | Simone et al. |
| 3,877,437 A | 4/1975 | Maitan et al. |
| 4,444,190 A | 4/1984 | Mutzhas |
| 4,712,014 A | 12/1987 | Eich |
| 4,839,513 A | 6/1989 | Wijtsma |
| 4,897,770 A | 1/1990 | Solomon |
| 5,597,231 A | 1/1997 | Rosset |
| 5,792,214 A | 8/1998 | Larsson et al. |
| 5,855,595 A | 1/1999 | Fujishima et al. |

FOREIGN PATENT DOCUMENTS

| | | |
|---|---|---|
| DE | 4037483 A1 | 5/1992 |
| DE | 196 47 676 | 5/1998 |
| DE | 197 40 592 | 3/1999 |
| EP | 0 371 381 | 11/1989 |
| EP | 0627243 A1 | 7/1994 |

Primary Examiner—John P. Lacyk
(74) Attorney, Agent, or Firm—Barnes & Thornburg

(57) ABSTRACT

A phototherapy apparatus which includes a filter unit that is coupled to a light generating unit. The light generating unit includes a plurality of light sources and an electrical control board which can regulate and control the power applied to the light sources so as to affect the wattage output of the light sources. The filter unit includes housing which contains a filter slide that is movable within the housing. The filter slide includes a plurality of filter elements and apertures which separate adjacent filter elements. The filter slide is movable between a first position in which light produced by the light generating unit passes through the apertures in the filter slide and a second position in light produced by the light generating unit passes through the filter elements in the filter slide.

29 Claims, 5 Drawing Sheets

PHOTOTHERAPY APPARATUS

BACKGROUND AND SUMMARY OF THE INVENTION

The present invention relates to a phototherapy apparatus for providing phototherapeutic treatment to new-born infant patients. More particularly, the present invention is directed to a phototherapy apparatus which can selectively provide different wavelengths of therapeutic light.

Hyperbilirubinemia, which occurs comparatively frequently in new-born, and particularly prematurely born infants, is a condition in which excessive bilirubin is in the blood. Hyperbilirubinemia results in an increase permeability of the blood-brain barrier. Accordingly, new-borns suffering from hyperbilirubinemia are susceptible to damage of their central nervous systems caused by the decomposition products of bilirubin in their brain cells.

Hyperbilirubinemia has been treated with chemotherapy and phototherapy. In the phototherapeutic treatment, new-borns are radiated with light in the visible spectrum range.

The present invention provides a phototherapy apparatus which allows for changing the wavelength of treatment radiation.

According to other features, characteristics, embodiments and alternatives of the present invention which will become apparent as the description thereof proceeds below, the present invention provides a phototherapy apparatus which includes a light generating unit having a plurality of light sources, a controller to control the power applied to the plurality of light sources, and a filter unit coupled to the light generating unit and including a filter slide which carries a plurality of filter elements that are separated by adjacent apertures. The filter slide is selectively positionable between a first position in which light emitted from the light generating unit does not pass through the plurality of filter elements and a second position in which light emitted from the light generating unit passes through the plurality of filter elements.

The present invention further provides a filter unit for a phototherapy apparatus which includes a housing that can be coupled to a light generating apparatus and includes a plurality of spaced apart apertures and a filter slide movable within the housing between a first and second position, the filter slide including a plurality of filter element which are separated by adjacent apertures. When the filter slide is in the first position, the apertures therein are aligned with the plurality of apertures in the housing. When the filter slide is in the second position, the plurality of filter elements are aligned with the plurality of apertures in the housing.

The present invention also provides a method of providing phototherapy to a patient which involves providing a phototherapy light generating unit and providing a filter unit which comprises a filter slide movable between a first and second position. The filter slide includes a plurality of filter elements which are separated by adjacent apertures. When the filter slide is in the first position, light passing through the filter unit does not pass through the plurality of filter elements. When the filter slide is in the second position, light passing through the filter unit passes through the plurality of filter elements. The method also includes coupling the filter unit to the phototherapy light generating unit, and moving the filter slide between the first and second position to change the wavelength of emitted light.

BRIEF DESCRIPTION OF DRAWINGS

The present invention will be described hereafter with reference to the attached drawings which are given as non-limiting examples only, in which.

DETAILED DESCRIPTION OF THE DRAWINGS

Figure 1:
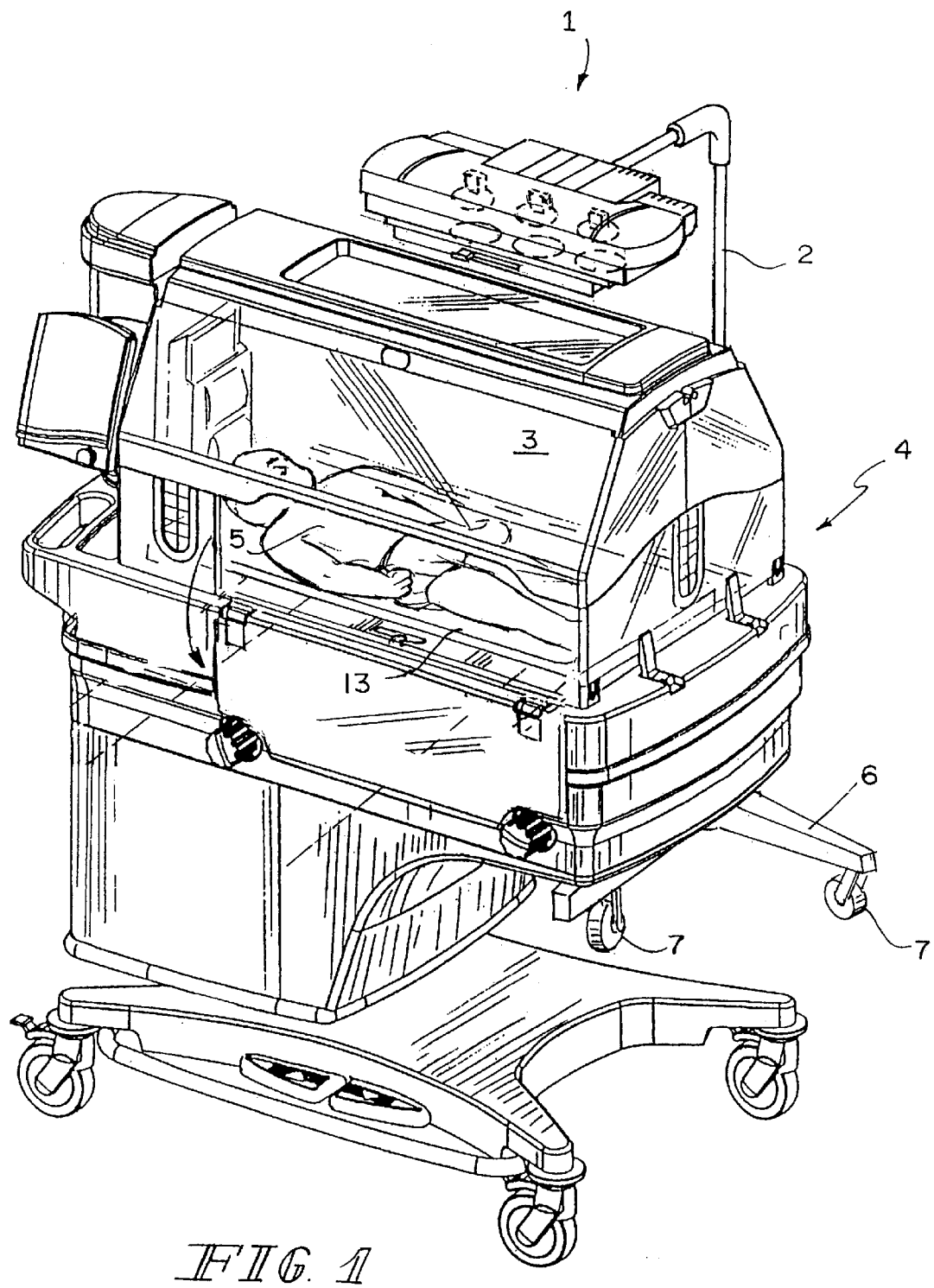
FIG. 1 is a perspective view of a phototherapy apparatus mounted on a stand and positioned over an incubator according to one embodiment of the present invention.

The present invention is directed to a phototherapy apparatus which can selectively provide different wavelengths of light for phototherapeutic treatment. The apparatus of the present invention includes a filter unit which is configured to be coupled to a light producing unit. The light generating unit includes a plurality of light sources and an electrical control board which can regulate and control the power applied to the light sources so as to affect the power output of the light sources.

The filter unit includes a housing which contains a filter slide that is movable within the housing. The filter slide includes a plurality of filter elements and apertures which separate adjacent filter elements. The filter slide is movable between first and second positions within the housing. When positioned in the first position, light produced by the light generating unit passes through the apertures in the filter slide.

When positioned in the second position, light produced by the light generating unit passes through the filter elements in the filter slide. According to one embodiment of the present invention white light in the range of about 300 to about 780 nm passes through filter unit when the filter slide is in its first position and blue light in the range of about 400 to about 600 nm passes through the filter unit when the filter slide is in its second position.

In order to adjust the power output of light which passes through the filter unit, the power to the light sources in the light generating unit is increased when the filter slide is in its second position. For example, according to one embodiment, the power to the light sources is controlled to provide a power output of about 50 watts when the filter slide was in its first position, and to provide a power output of about 75 watts when the filter slide was in its second position. As can be understood, the increase in output power of the light sources compensates for the loss of intensity as the light passes through the filter elements in the filter slide.

According to one embodiment of the present invention, the filter unit can include switches which detect when the filter slide is in the first or second position. Such switches can be electrically coupled to the electrical control board which in turn can adjust the power to the light sources depending on the detected position of the filter slide.

The phototherapy apparatus of the present invention can include a display which can be used to indicate type of therapeutic light being emitted. In addition, a timer can be incorporated to control the duration of phototherapeutic treatment. It is to be understood that different light sources can be used in the light generating unit and different filters can be used in the filter unit so as to produce desired wavelengths of therapeutic light.

While the preferred embodiment of the filter unit is movable between first and second positions as described herein, it is within the scope of the present invention to provide a filter unit movable to a third position at which light produced by the light generating unit passes through a second series of filter elements in the filter slide to produce therapeutic light at a second desired wavelength, thereby providing a caregiver with an alternative therapy choice. Furthermore, it is within the scope of the present invention to provide a filter unit including four or more positions to accommodate additional series of filters if such is desired to further increase the therapeutic choices available to the caregiver. Finally, it is within the scope of the present invention to provide a filter unit including a filter, a lens, or a series of in-line lenses that are adjustable relative to one another in order to manipulate the wavelength of the light provided by the phototherapy apparatus. In each embodiment of the invention, the power to the light sources in the light generating unit is adjusted in order to compensate for the changes in intensity as the light passes through the filter elements in the filter slide.

In addition, while the preferred embodiment of the present invention simply adjusts the power to the light sources in the light generating unit in response to the position of the filter slide, it is within the scope of the present invention to include a controller configured to control the power to the light sources in the light generating unit and a sensor configured to sense the intensity of the light once it has passed through the filter unit, the sensor providing a signal to the controller in response to the intensity of light sensed by the sensor. In such configuration, the controller causes the power to the light sources in the light generating unit to increase or decrease until the intensity of light sensed by the sensor reaches a desired intensity. Such a sensor could be located adjacent the infant receiving phototherapeutic treatment, adjacent the light generating unit, or at any location at which the intensity of the therapeutic light can be detected desired by the user.

FIG. 1 is a perspective view of a phototherapy apparatus mounted on a stand and positioned over an incubator according to one embodiment of the present invention. The phototherapy apparatus generally identified by reference numeral 1 is depicted as being mounted on a stand 2 so as to be positioned over a transparent window 3 of an incubator 4 in which an infant 5 is positioned on a mattress 13. The phototherapy apparatus 1 produces therapeutic light that shines through transparent window 3 and onto the infant 5. The stand 2 depicted in FIG. 1 includes a base 6 that is supported on casters 7. The use of a movable base 6 will allow the phototherapy apparatus 1 to be used with various incubators, cribs, and other infant supporting devices, including various therapy platforms. In an alternative embodiment, the incubator 4 can be provided with a pole mount (not shown) in which stand 2 could be received and held.

Figure 2:
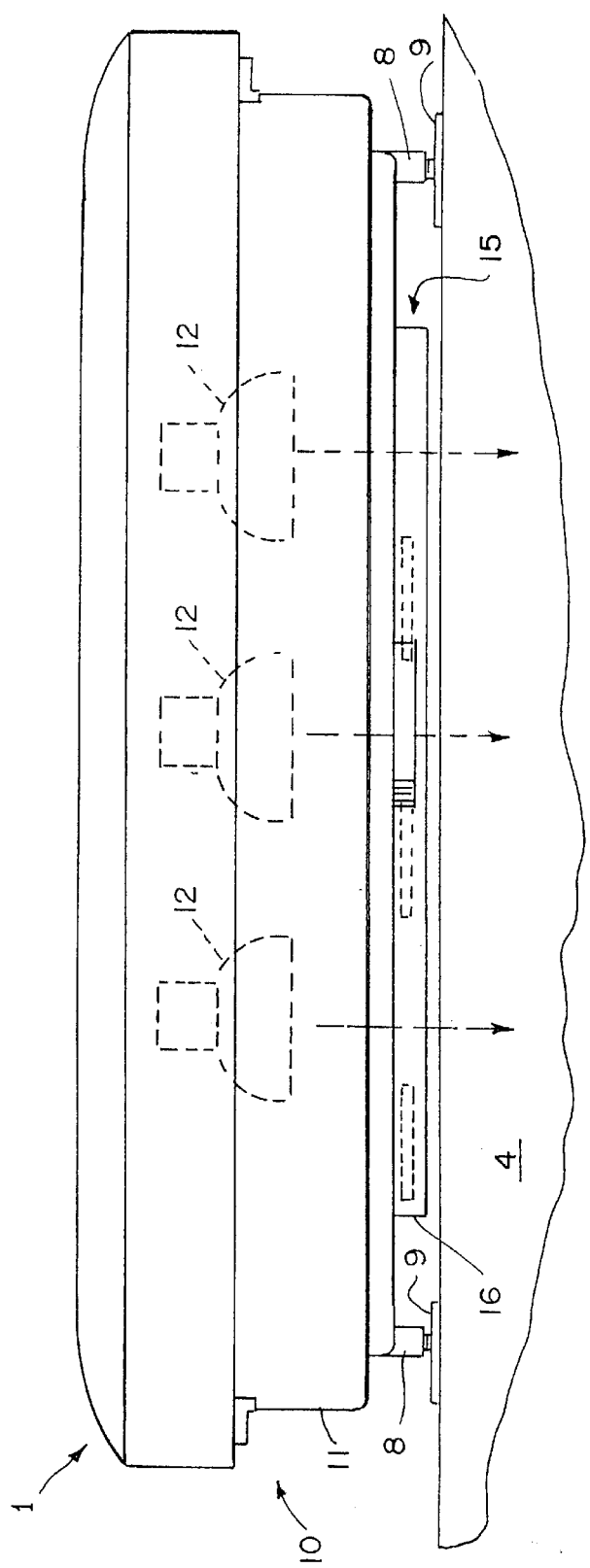
FIG. 2 is a side elevation view of a phototherapy apparatus positioned on top of the incubator according to another embodiment of the present invention.

FIG. 2 is a side elevation view of a phototherapy apparatus positioned on top of the incubator according to another embodiment of the present invention. The phototherapy apparatus 1 depicted in FIG. 2 includes a plurality of legs 8 upon which the phototherapy apparatus 1 can rest on top of the incubator 4. The legs 8 can include bases 9 which can be suction cups or similar devices that will prevent the phototherapy apparatus 1 from moving once positioned on incubator 4. In further embodiments, other structure such as recesses or posts for receiving legs 8 can be incorporated into the top of incubator 4 and/or bottom of phototherapy apparatus 1.

The light producing unit 10 includes a housing 11 and a plurality of light sources 12 which are depicted in phantom. A filter unit 15 is coupled to the light producing unit 10. The filter unit 15 includes a housing 16 which is attached to the light producing unit 10 and a filter slide 34 (see FIG. 4) which is movable within housing 16.

The housing 16 of the filter unit 15 includes a plurality of apertures 36 (see FIG. 4) which are equal in number to and aligned with the plurality of light sources 12. However, it is within the scope of the invention as presently perceived to provide housing 16 with either fewer apertures or more apertures than the number of light sources 12 in order to provide any desired lighting characteristics.

The filter slide 34 includes a plurality of apertures 36 (see FIG. 4) formed therein and a plurality of filter elements 38. The apertures 36 and filter elements 38 are alternatively arranged and aligned so that when the filter slide 34 is moved in a first position, the light sources 12, apertures 36 in the filter slide 34 and apertures 30 in the housing 16 of the filter unit 15 are aligned so that unfiltered light is delivered to a patient. When the filter slide 34 is moved in a second position, the light sources 12, filter elements 38 in the filter slide 34 and apertures 30 in the housing 16 of the filter unit 15 are aligned so that filtered light is delivered to a patient.

The light sources 12 produce light that shines through the plurality of apertures 30 of the housing 16 of the filter unit 15. The number of light sources should be equal in number to the apertures 30. Although three light sources 12 and three apertures 30 are depicted, it is to be understood that any number of light sources 12 and apertures 30 could be used in order to effect a desired uniformity of patient irradiation. The numbers of filter elements 38 provided in the filter slide 34 should be equal in. number to the number of light sources 12 and apertures 30 in the housing 16. The number of apertures 36 provided in the filter slide 34 should be one less than the number of light sources 12 and apertures 30 in the housing 16. While filter slide 34 of the preferred embodiment provides one less aperture 36 in filter slide 34 than the number of apertures 30 in housing 16, it is within the scope of the invention as presently perceived to provide filter slide 34 with either the same number of apertures 36 or more apertures 36 than the number of apertures 30 in housing 16. Likewise, it is within the scope of the invention as presently perceived to provide filter slide 34 with either fewer filter elements 38 or more filter elements 38 than the number of apertures 30 in housing 16. Thus, for example, if filter slide 34 includes fewer apertures 36 than the number of apertures 30 in housing 16 and filter slide 34 includes the same number of filter elements 38 as the number of apertures 30 in housing 16, then the increase in output power of the light sources to compensate for the loss of intensity as light passes through filter elements 38 may be less than would be required if filter slide 34 included the same number of apertures 36 as filter elements 38.

Figure 3:
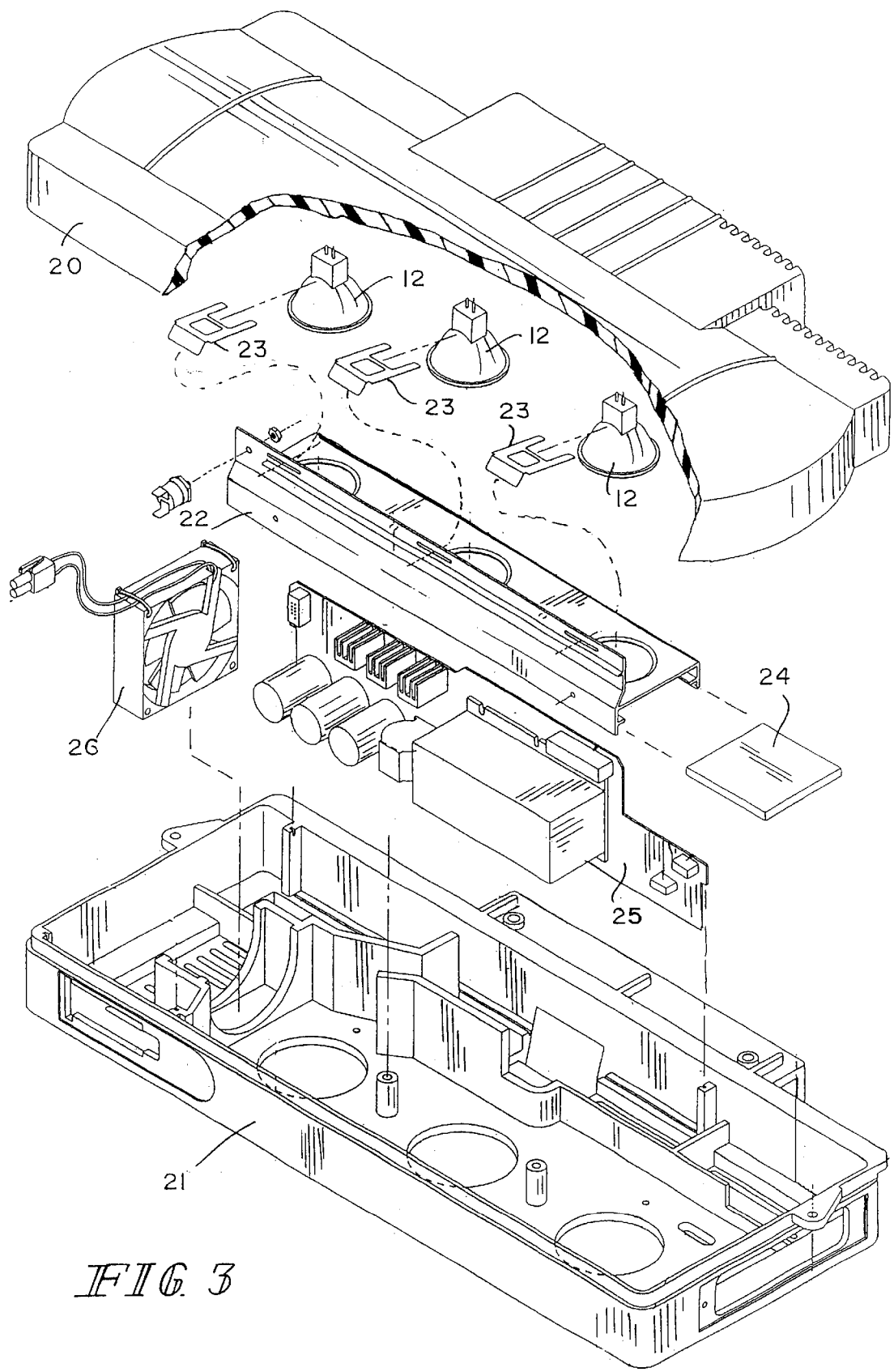
FIG. 3 is an exploded perspective view of a phototherapy apparatus according to the present invention.

FIG. 3 is an exploded perspective view of the phototherapy apparatus according to the present invention. FIG. 3 depicts the light producing unit 10 as including a housing which includes upper and lower halves 20 and 21 which can be coupled together in any convenient manner. Three light sources 12 are depicted as being coupled to support 22 by means of mechanical clips 23 which allow the light sources 12 to be easily removed and replaced. In the embodiment of the invention depicted in FIG. 3, a single or a plurality of glass plates 24 can be provided beneath light sources 12 to shield the light sources 12. As depicted, the glass plate(s) 24 can be held by support 22 or otherwise by lower housing half 21.

The light producing unit 10 includes a control board 25 that is electrically coupled to the light sources 12. The light producing unit 10 also includes a fan 26 that is electrically coupled to the control board 25 and positioned to cool the light sources 12 during operation.

Figure 4:
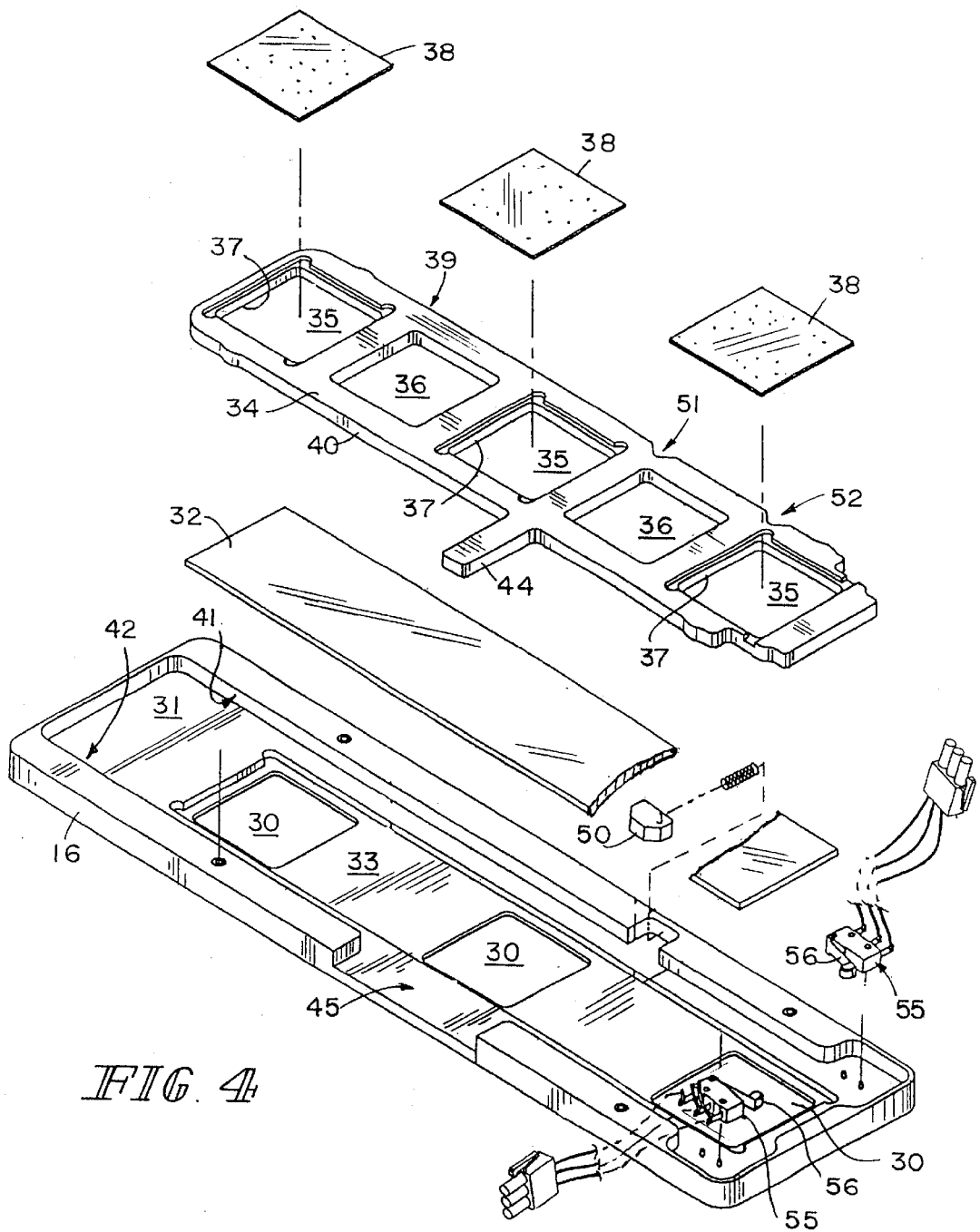
FIG. 4 is an exploded perspective view of the filter unit for the phototherapy apparatus according to one embodiment of the present invention.

FIG. 4 is an exploded perspective view of the filter unit for the phototherapy apparatus according to one embodiment of the present invention. The housing 16 of the filter unit 15 depicted in FIG. 4 includes three apertures 30 which are formed in a central recessed portion 31 of the housing 16. An elongated ultraviolet filter plate 32 is positioned over the three apertures 30. The ultraviolet filter plate 32 can be received in an additional recess 33 which is sized to hold the ultraviolet filter plate 32 over apertures 30 which are formed in housing 16.

The filter slide 34 includes a plurality of apertures 35 and 36. Apertures 35 have recessed edges 37 for receiving filter elements 38. It is herein noted that the use of recesses for holding and securing the various elements, including the ultraviolet filter plate 32, filter slide 34 and filter elements 38 is sufficient due to the manner in which the filter unit 15 is coupled to the outer surface of the lower housing half 21 of the light producing unit 10. That is the various elements, including the ultraviolet filter plate 32, filter slide 34 and filter elements 38 are sandwiched together in the final assembly.

It is noted that in the illustrated embodiment there are filter elements 38 provided at either end of the filter slide 34 so that there is one less aperture 36 than the number of filter elements 38. As will be understood from the description of the invention presented below in reference to FIGS. 5 and 6, when the filter slide 34 is moved in a position in which the apertures 36 thereof are aligned with the apertures 30 formed in the filter housing 16, the gap provided between the end of filter slide 34 and the end of central recess 31 functions as an aperture to allow light from an aligned light source 12 to pass therethrough. As noted above, according to further embodiments of the present invention, the filter slide 34 can be provided with either the same number of apertures 36 or more apertures 36 than the number of apertures 30 in housing 16. Likewise, it is within the scope of the invention as presently perceived to provide filter slide 34 with either fewer filter elements 38 or more filter elements 38 than the number of apertures 30 in housing 16.

The central recess 31 which is formed in housing 16 is sized to receive filter slide 34 so that filter slide 34 can move within central recess 31 in the manner discussed in more detail below. As depicted, the filter slide 34 has a generally rectangular shape with sides 39 and 40 which are guided along sides 41 and 42 of central recess 31. The filter slide 34 includes a handle or lever 44 which extends from a side portion thereof. The handle or lever 44 is received in a cut-out portion 45 of the housing 16 which extends into the central recess 31 as shown.

The position of the filter slide 34 is controlled by a detent mechanism which includes a spring biased latch element 50 and notches 51 and 52 which are provided in a side 39 of filter slide 34. The spring biased latch element 50 is positioned in side wall 41 of the central recess 31, whereat it can engage notches 51 and 52 as the filter slide 34 moves within central recess 31. Notches 51 and 52 and spring biased latch element 50 are shaped in such a manner that engagement of the latch element 50 with either notch 51 or 52 can be overcome by sliding filter slide 34 under moderate pressure. In this regard, the engaging face of the spring biased latch element 50 includes angled leading and trailing edges, and notches 51 and 52 have corresponding angled surfaces which allow the spring biased latch element 50 to be pushed out of engagement as the respective angled surfaces slide along one another. It is to be understood that angled and/or curved surfaces could be used on the spring biased latch 50 and notches 51 and 52. Also, it is to be understood that the spring biased latch element 50 could be provided on the filter slide 34 and the notches 51 and 52 could be provided in the sides of the central recess 31 in filter housing 16. In addition, a single notch and two spring biased latch elements could also be used according to the present invention.

One end of the filter housing 16 is provided with a pair of switches 55 that are electrically coupled to control board 25. Switches 55 include trip arms 56 and are positioned so that the trip arms 56 are engaged by the filter slide 34 when the filter slide 34 is moved toward the end of the filter housing 16 which contains switches 55. Switches 55 are electrically coupled to control board 25 and used to moderate the power applied to the light sources 12 so that, according to one embodiment, the wattage output of the light sources is increased when filter elements 38 are positioned to filter light emitted from the light sources 12.

Figures 5, 6:
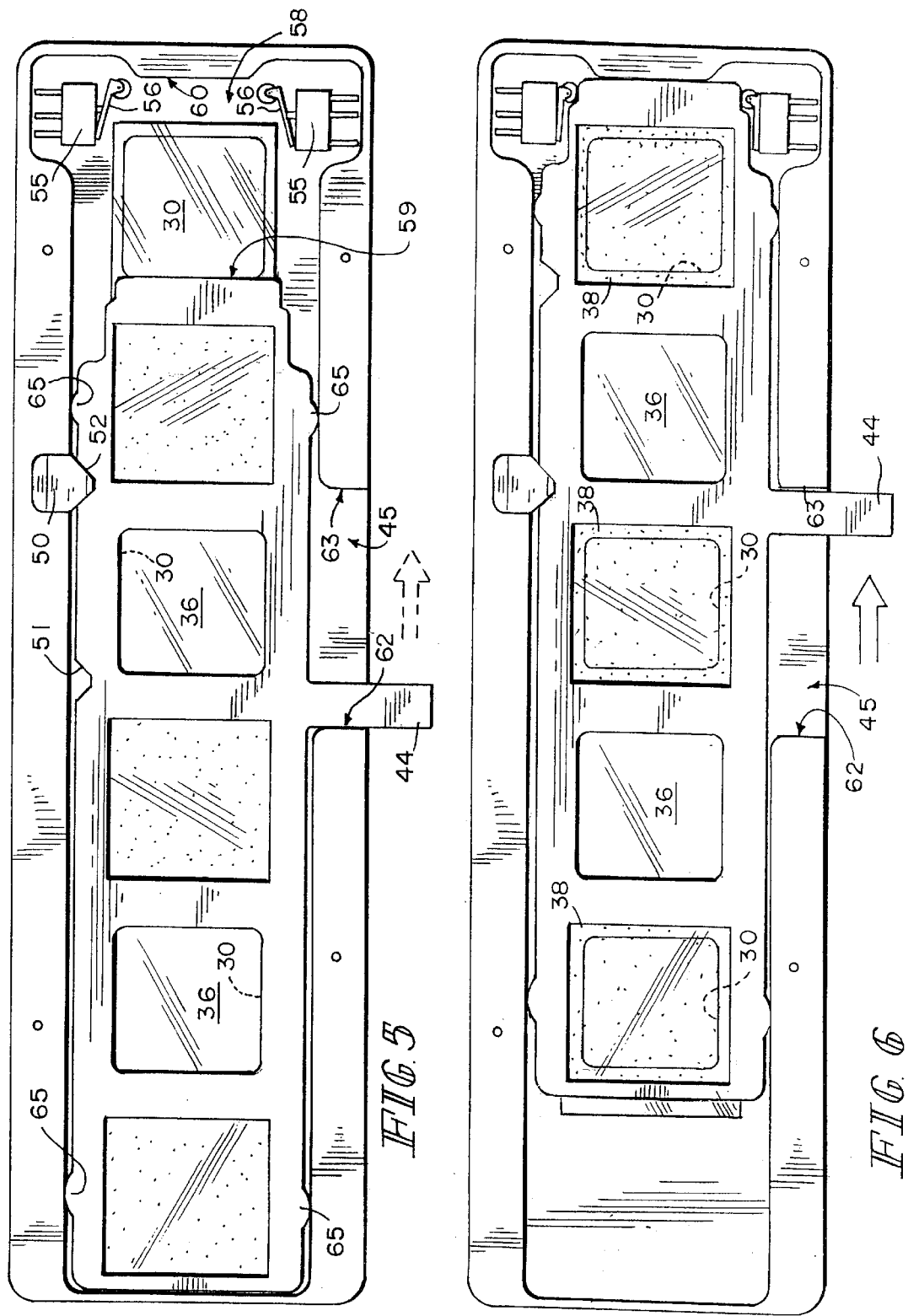
FIG. 5 is a top plan view of the filter unit of FIG. 4 showing the slide shifted to the left to hold the filters in the first position so that light does not pass through the filters.
FIG. 6 is a top plan view similar to FIG. 5 showing the slide shifted to the right so that the filters are positioned in the second position over the apertures to filter light which passes through the apertures.

FIG. 5 is a top plan view of the filter unit of FIG. 4 showing the filter slide shifted into a first position in which light does not pass through the filters. As shown, when the filter slide 34 is moved, i.e., slid into the position depicted in FIG. 5, the apertures 36 in the filter slide 34 are aligned with the apertures 30 in the housing 16 of the filter unit 15 so that light emitted from the light sources 12 passes through the aligned apertures 36 and 30 and not through filter elements 38.

The filter slide 34 is shorter in length than central recess 31 so that, when the filter slide 34 is in the position depicted in FIG. 5, there is a gap 58 between the lead end 59 of filter slide 34 and the end 60 of central recess 31. This gap 58 coincides with the last aperture 30 which is formed in housing 16 of filter unit 15, so that when the filter slide 34 is in the position depicted in FIG. 5, light emitted from light sources 12 can pass through the last aperture 30 formed in housing 16.

In order to properly position filter slide 34 so that the apertures 36 of the filter slide 34 are aligned with the apertures 30 in the housing 16 of the filter unit 15, the cut-out portion 45 of the slide 42 of the housing 16 which extends into the central recess 31 has a first end wall 62 positioned to stop movement of handle or lever 44 at a location that properly aligns apertures 36 and 30, as depicted. In addition, lead notch 52 is formed in the side 39 of filter slide 34 at a location whereat when spring biased latch 50 is engaged therewith, the apertures 36 of the filter slide 34 are aligned with the apertures 30 in the housing 16 of the filter unit 15. In addition to properly positioning filter slide 34, detent mechanism also holds the filter slide 34 in the position depicted in FIG. 5.

FIG. 5 depicts filter slide 34 as including side protrusions 65 that can be included to reduce the surface contact between the sides of filter slide 34 and the sides of central recess 31, while aligning filter slide 34 for movement in central recess 31.

The lead end 59 of the filter slide 34 is configured to engage trip arms 56 of switches 55 which are positioned near the end of the central recess 31. For switches 55 which have trip arms 56 as illustrated, the lead end 59 of the filter slide 34 can be configured to have stepped shaped edges as depicted. This stepped shape can engage and trip arms 56 of switches 55 as shown in FIG. 6.

FIG. 6 is a top plan view similar to FIG. 5 showing the slide shifted to the right so that the filters are positioned in the second position over the apertures to filter light which passes through the apertures. As shown, when the filter slide 34 is moved, i.e., slide into the position depicted in FIG. 6, the filter elements 38 in the filter slide 34 are aligned with the apertures 30 in the housing 16 of the filter unit 15 so that light emitted from the light sources 12 pass through the filter elements 38 and apertures 30.

From a comparison of FIGS. 5 and 6 it can be seen that the filter slide 34 is moved in FIG. 6 a distance equal to the gap 58 which is present in FIG. 5. In order to properly position filter slide 34 so that the filter elements 38 of the filter slide 34 are aligned with the apertures 30 in the housing 16 of the filter unit 15, the cut-out portion 45 of the filter slide 34 which extends into the central recess 31 has a second end wall 63 positioned to stop movement of handle or lever 44 at a location that properly aligns filter elements 38 and apertures 30, as depicted. In addition, the second notch 51 is formed in the side 39 of filter slide 34 at a location whereat when spring biased latch 50 is engaged therewith, the filter elements 38 of the filter slide 34 are aligned with the apertures 30 in the housing 16 of the filter unit 15. In addition to properly positioning filter slide 34, detent mechanism also holds the filter slide 34 i n the position depicted in FIG. 6.

FIG. 6 depicts the stepped shape lead end 59 of the filter slide 34 in engagement with the trip arms 56 of switches 55. It is to be understood that other types of switches could be used including optical, mechanical and electrical switches and that the lead end 59 of the filter slide 34 could be configured to activate such other switches.

In use, the filter housing 16 is coupled to the light, producing unit 10 and the assembly is positioned over a patient by mounting the assembly on a stand as depicted in FIG. 1 or by mounting the assembly directly on an incubator as depicted in FIG. 2. Depending on the desired wavelength of phototherapeutic light to be used, the filter slide 34 is either moved to the first position in which light generated by the light sources 12 only passes through the ultraviolet filter plate 32 (see FIG. 4), or is otherwise moved to the second position in which light generated by light sources 12 passes through filter elements 38.

As the filter slide is moved between its first and second position, switches 55 are used to detect the position of filter slide 34. In response to such detection, control board 25 can be used to moderate the power supplied to the light sources 12 so that, according to one embodiment, the output wattage of the light sources 12 is increased when filter elements 38 are positioned to filter light emitted from the light sources 12. The use of two switches 55 provides a safety redundancy to ensure that a patient will not be exposed to too much or too strong of irradiation.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A phototherapy apparatus which comprises:
   a light generating unit having a plurality of light sources and a controller to control the power applied to the plurality of light sources; and
   a filter unit coupled to the light generating unit and including a filter slide which carries a plurality of filter elements that are separated by adjacent apertures, the filter slide being selectively positionable between a first position in which light emitted from the light generating unit does not pass through the plurality of filter elements and a second position in which light emitted from the light generating unit passes through the plurality of filter elements.

2. A phototherapy apparatus according to claim 1, wherein the filter unit includes a housing in which the filter slide moves between the first and second position and a detent mechanism which engages when the filter slide is in the first and second positions.

3. A phototherapy apparatus according to claim 2, wherein the filter slide includes a lever which extends through a side of the filter unit housing, the lever being provide for moving the filter slide between the first and second positions.

4. A phototherapy apparatus according to claim 1, wherein the filter unit further includes at least one switch which is activated when the filter slide is moved into the second position, the switch being in electrical communication with the means to control power applied to the plurality of light sources.

5. A phototherapy apparatus according to claim 1, wherein the filter unit further includes an ultraviolet filter which extends adjacent to the plurality of filter elements and adjacent apertures.

6. A phototherapy apparatus according to claim 1, wherein the number of filter elements in the filter slide is greater than the number of adjacent apertures.

7. A phototherapy apparatus according to claim 6, wherein the number of filter elements is equal to the number of light sources.

8. A phototherapy apparatus according to claim 2, wherein the housing of the filter unit includes a plurality of apertures which are equal in number to the number of filter elements.

9. A phototherapy apparatus according to claim 2, wherein the light generating unit includes a plurality of apertures though which light generated by the plurality of light sources passes.

10. A phototherapy apparatus according to claim 1, wherein the plurality of filter elements and adjacent apertures are rectangular.

11. A phototherapy apparatus according to claim 1, wherein the light generating unit includes a plurality of feet.

12. A filter unit for a phototherapy apparatus which comprises:
   a housing that can be coupled to a light generating apparatus and includes a plurality of spaced apart apertures; and
   a filter slide movable within the housing between a first and second position, the filter slide including a plurality of filter elements which are separated by adjacent apertures, wherein when the filter slide is in the first position, the apertures therein are aligned with the plurality of apertures in the housing and when the filter slide is in the second position, the plurality of filter elements are aligned with the plurality of apertures in the housing.

13. A filter unit for a phototherapy apparatus according to claim 12, further including a detent mechanism which engages when the filter slide is in the first and second positions.

14. A filter unit for a phototherapy apparatus according to claim 13, wherein the filter slide includes a lever which extends through a side of the filter unit housing, the lever being provide for moving the filter slide between the first and second positions.

15. A filter unit for a phototherapy apparatus according to claim 12, further including means for detecting when the filter slide is in the second position.

16. A filter unit for a phototherapy apparatus according to claim 12, wherein the filter unit further includes an ultraviolet filter which extends adjacent to the plurality of filter elements and adjacent apertures.

17. A filter unit for a phototherapy apparatus according to claim 12, wherein the plurality of filter elements and adjacent apertures are rectangular.

18. A method of providing phototherapy to a patient which comprises:
    providing a phototherapeutic light generating unit;
    providing a filter unit which comprises a filter slide movable between a first and second position, the filter slide including a plurality of filter elements which are separated by adjacent apertures, wherein when the filter slide is in the first position, light passing through the filter unit does not pass through the plurality of filter elements and when the filter slide is in the second position, light passing through the filter unit passes through the plurality of filter elements;
    coupling the filter unit to the phototherapy light generating unit; and
    moving the filter slide between the first and second position to change the wavelength of emitted light.

19. A method of providing phototherapy to a patient according to claim 18, wherein the phototherapeutic light generating unit includes a plurality of light sources and the method further comprises:
    changing the power applied to the plurality of light sources when the filter slide is moved between the first and second positions.

20. A method of providing phototherapy to a patient according to claim 19, wherein the filter unit includes means for detecting when the filter slide is in the second position and the step of changing power to the plurality of light sources comprises detecting when the filter slide is in the second position and in response thereto, changing power to the plurality of light sources.

21. A phototherapy apparatus comprising:
    a light source;
    a filter unit movable between a first position for allowing light from the light source that encompasses a first range of wavelengths to pass therethrough and a second position for allowing light from the light source that encompasses a second range of wavelengths to pass therethrough; and
    an electrical control board coupled to the light source that adjusts power applied to the light source in response to the position of the filter unit.

22. A phototherapy apparatus comprising:
    a light source;
    an electrical control board coupled to the light source; and
    a filter unit including a switch coupled to the electrical control board and providing a switch signal thereto, the electrical control board controlling the power applied to the light source in response to the switch.

23. The phototherapy apparatus of claim 22, wherein the filter unit is movable between a first position and a second position and the switch signal indicates the position of the filter unit.

24. The phototherapy apparatus of claim 23, wherein the filter unit includes a housing and a filter slide movable relative to the housing between a first slide position and a second slide position, the filter unit being in the first position when the filter slide is in the first slide position and the filter unit being in the second position when the filter slide is in the second slide position.

25. A phototherapy apparatus for providing light at a desired intensity, the phototherapy apparatus comprising:
    a light source;
    a therapy platform positioned to lie beneath the light source for carrying an infant;
    a filter unit interposed between the light source and the therapy platform; and
    an electrical control board coupled to the light source, the electrical control board adjusting power output of the light source so that an intensity of light at the therapy platform remains generally constant.

26. A phototherapy apparatus for providing light at a desired intensity, the phototherapy apparatus comprising:
    a light source;
    a therapy platform positioned to lie beneath the light source for carrying an infant;
    filtering means interposed between the light source and the therapy platform for adjusting a range of wavelengths of light transmitted from the light source to the therapy platform; and
    adjusting means for adjusting power output of the light source in response to the range of wavelengths transmitted to the therapy platform.

27. The phototherapy apparatus of claim 26, wherein the adjusting means includes means for maintaining the intensity of light at the therapy platform at a generally constant intensity.

28. A phototherapy apparatus comprising:
    a light producing unit;
    a filter unit movable between a first position and a second position; and
    a switch coupled to the filter unit and coupled to the light producing unit, the switch being moved to a first switch position when the filter unit is in the first position and the switch being moved to a second switch position when the filter unit is in the second position, the light producing unit emitting light at a first power output when the switch is in the first switch position and the light producing unit emitting light at a second power output when the switch is in the second switch position.

29. An incubator comprising:
    a mattress; and
    a phototherapy apparatus configured to deliver light having a desired intensity to the mattress, the phototherapy apparatus including:
        a light producing unit for producing light at a selected intensity; and
        an adjustable filter unit interposed between the light producing unit and the mattress, the light producing unit adjusting the intensity of light delivered to the filter unit so that the intensity of light delivered to the mattress is at the desired intensity.

* * * * *